United States Patent [19]

Claracq

[11] Patent Number: 4,586,501
[45] Date of Patent: May 6, 1986

[54] DEVICE FOR PARTLY OCCLUDING A VESSEL IN PARTICULAR THE INFERIOR VENA CAVA AND INHERENT COMPONENT OF THIS DEVICE

[76] Inventor: Michel Claracq, 17, rue de Vittel, 31300 Toulouse, France

[21] Appl. No.: 543,272

[22] Filed: Oct. 19, 1983

[30] Foreign Application Priority Data

Oct. 21, 1982 [FR] France .............................. 82 17766

[51] Int. Cl.⁴ .............................................. A61B 17/12
[52] U.S. Cl. .................................... 128/325; 128/326; 128/346
[58] Field of Search ............... 128/325, 326, 327, 346, 128/DIG. 25; 24/463, 481

[56] References Cited

U.S. PATENT DOCUMENTS

| | | | |
|---|---|---|---|
| 3,538,917 | 5/1970 | Selker | 128/326 |
| 3,675,656 | 7/1972 | Hakim | 128/325 |
| 3,730,186 | 11/1973 | Edmunds et al. | 128/325 |
| 3,746,002 | 7/1973 | Haller | 128/346 |
| 4,112,951 | 9/1978 | Hulka et al. | 128/325 |

*Primary Examiner*—Robert Peshock
*Assistant Examiner*—Cary E. Stone
*Attorney, Agent, or Firm*—Harold H. Dutton, Jr.

[57] ABSTRACT

The invention concerns a device partly occluding a vessel, of the type comprising a clip provided with teeth and designed to externally straddle the vessel. In the invention, the clip teeth are retractable, consisting notably of one or more flexible membranes which can be pressurized to array the teeth in projection in the active position or on the contrary which can be depressurized to withdraw the teeth and to put them in the passive position; the clip is associated with remote controls 2, 3 whereby the teeth can be put either into the active or into the passive position. These controls consist in particular of a catheter 3 and a hydraulic member pressurizing or depressurizing the clip membranes.

19 Claims, 15 Drawing Figures

FIG. 7
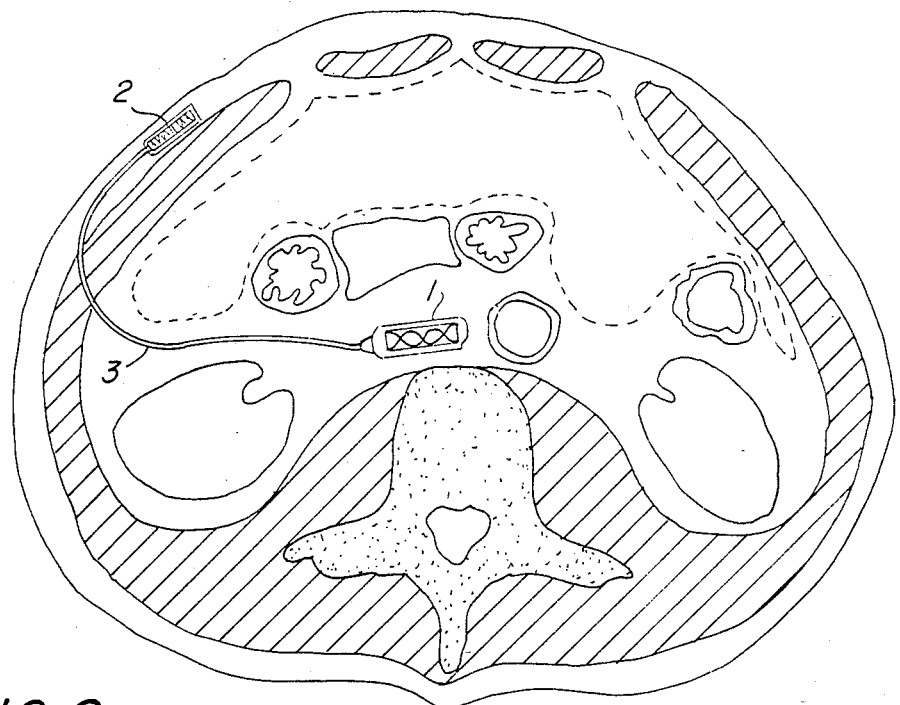
FIG. 8a
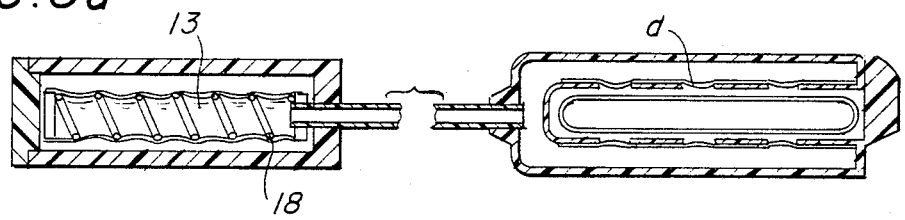
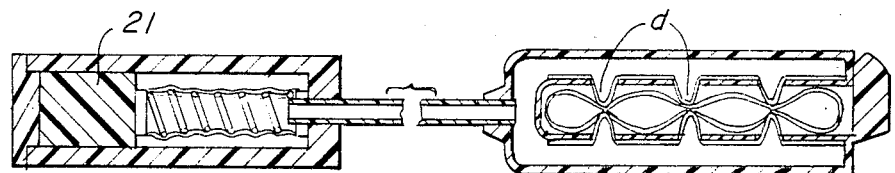
FIG. 8b
FIG. 9
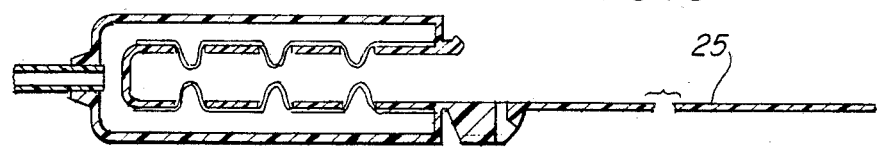

DEVICE FOR PARTLY OCCLUDING A VESSEL IN PARTICULAR THE INFERIOR VENA CAVA AND INHERENT COMPONENT OF THIS DEVICE

This invention relates to a device for partly occluding the caudal vena cava (or inferior vena cava) of a sick person in order to suppress the fatal risk of certain pulmonary embolisms. The invention is not restricted to occluding the vena cava, and within medicine, surgery and possibly the veterinary art, it also extends to occluding any vessel.

BACKGROUND AND OBJECTS

It is known that because of its frequency and gravity, pulmonary embolism is a major medical problem; it threatens any patient suffering from phlebitis in the limbs in spite of frequently applied preventative or healing medical treatment. The nearly sole origin of embolism is in the venous network of the lower limbs and the pelvis, possibly with thrombosis extension in the caudal vena cava. Already for a long time the idea has been entertained to obstruct the caudal vena cava to block the migration of the clot or embolus toward the heart and hence toward the lungs.

Initially the obstruction was realized by mere ligature of the sub-renal caudal vena cava, but this technique suffers from the drawback of precipitating in every case a massive thrombosis of the venous segment upstream of the ligature (due to the totality of the occlusion).

Therefore total ligature has been given up in favor of a partial blockage of the caudal vena cava. Presently two modes of the latter technique are being applied:

(a) either this partial blockage is placed inside the vein (filter, screen or other), which is a technique offering the advantage not to require general anesthesia but incurs the serious drawback of the risk of thrombosis upstream of the blockage and practically as large as in the case of total ligature (in particular due to introducing a foreign body into the vessel), or (b) placing an external and so-called extra-venous member around the vein, straddling the vein and partitioning its inside aperture into several channels of lesser bores.

The object of the present invention is a technique of the latter type wherein the partial occlusion of the vein or more generally of the vessel is achieved from its outside. An essential advantage of this technique is the appreciable reduction of risks of thrombosis.

The most improved and widely used device to implement this technique presently is a clip, in particular the ADAMS & DE WEESE clip developed in 1966; this polytetrafluoroethylene-molded clip comprises two arms forming a U, one of which is serrated. This clip is put in place on the vein so its two arms will straddle it and then is finally closed by a filament which binds said arms at their free ends (which ends are provided with notches for this purpose). The vein walls therefore are deformed and the presence of the teeth imparts to the inside aperture of the vein a partitioned shape, partly sealed, capable of stopping large clots or emboli while allowing the blood to circulate in the lesser cross-sectional channels (which are bounded by the clip teeth). In this manner dangerous pulmonary embolisms are prevented satisfactorily.

Nevertheless this device incurs a serious drawback. Its emplacement must be considered final, because new surgery to remove the clip would be much more dangerous; besides the typical risks of general anesthesia and the risks of thrombosis in any intervention, such new surgery would be applied to mauled tissues whereby the patient might incur serious wounds in the vein. Moreover if in spite of these dangers the clip were removed, at the end of the embolism period, it would practically be out of the question to resort to a third intervention to put in place another in the event subsequent pathology were to demand another emplacement of a partial occlusion; in that case the sick (who is especially vulnerable) would be defenseless against an embolic accident (or else be forced to resort to an intravenous occlusion technique with its own drawbacks).

Under these conditions the clip put in place in final form on the patient provides a partial but indefinite blockage the patient carries with him all his life. Now it has been found that the blockage subjects the patient to dangers related to permanent blood stasis upstream of the clip so long as it is in place (that is, well after the embolic period of the patient and all his life); chronic venous insufficiency syndrome in the lower limbs and danger of delayed thrombosis. This is the major drawback of the ADAMS & DE WEESE clip and of the analogue clips presently existing.

An object of the present invention to remedy this defect and to provide an improved device for partial occlusion and resorting to an extra-venous technique.

The main object of the device is to provide a device capable of preventing pulmonary embolism during the embolic period while allowing nevertheless to eliminate after this period the above cited delayed dangers.

To that end the object of the invention is to provide a device capable of providing a temporary partial occlusion of a vessel and of allowing the elimination of this occlusion at the selected time, and to do so without deep intervention (in particular without having to subject the patient to general anesthesia and without having to work again near the vena cava on previously mauled tissue).

Another object of the invention is to repeat the occlusion effect after it was eliminated, at will, as many times as found necessary, in particular in the event of new pathology and to do this, as before, without deep intervention.

Another object of the invention is to facilitate the emplacement of the occluding member on the vessel.

BRIEF DESCRIPTION OF THE INVENTION

To that end, the partial occluding device object of this invention is of the type comprising a serrated clip designed to externally straddle the vessel to partition the internal aperture into several channels; in the present invention the clip teeth are retractable and associated with remote control means fitted to move them between an active position wherein said projecting teeth are capable of partitioning the vessel and a passive position wherein they are pulled back without noticeable effect on the vessel.

In a manner known per se, the clip is designed in particular to have two rigid or semi-rigid arms forming a U-shape with a double elbow part so as to be like a tuning fork, said arms comprising compression walls located opposite the vessel with which they will make contact; in the light of the features of the present invention, at least one of the clip arms being hollow and forming an inside chamber, the compression wall of each hollow arm comprising apertures; at least one flexible membrane is associated with the arms so as to seal the apertures of the compression walls, said membrane(s) being fitted to be placed by means of inflation across the apertures in order to constitute the active position teeth or by means of deflation to withdraw into the compression wall to provide the passive position of said teeth, the remote control means comprising devices for pressurizing or depressurizing the inside chamber of each hollow arm and are designed to generate upon actuation the inflation or deflation of the teeth.

Therefore, in the case of pulmonary embolism danger, the surgeon puts the clip of the invention in a location similar to that of the ADAMS & DE WEESE clip; during the emplacement, the clip teeth are in the passive (retracted) position which facilitates slipping the clip in place so it straddles the vessel. The surgeon frees the teeth by acting on remote controls whereby the partial occlusion function is filled, the vein being partitioned by the projecting teeth into several parallel channels of lesser bores.

At the end of the embolism period, it suffices to actuate again the remote controls to retract the teeth into their passive position without having to remove the clip and consequently without deep intervention as low as the vena cava. Thereupon the partitioning effect is eliminated and the stasis upstream of the vein is entirely removed, as well as all the risks it entails.

If thereafter the patient is subjected to no new embolism danger, the clip will be left in its passive state which allows normal blood circulation without upstream stasis. If on the other hand a new pathological event were to induce new dangers of embolism, the remote controls would be actuated again to put the teeth into their active position until this new embolism period is over.

The present invention applies to any type of retracting teeth and to any remote controls. However, the membrane embodiment with pressurized application and depressurized retraction appears advantageous in the light of its structural simplicity and its reliability of operation.

In this embodiment mode, the remote controls comprise preferably a catheter connected to the internal chamber of each hollow arm and a hydraulic or pneumatic member connected to the other end of said catheter and designed to generate the pressurization or depressurization of the inside chambers.

In particular the hydraulic or pneumatic member mentioned above may consist, on one hand, of a deforming fluid reservoir of variable capacity arranged to form together with the catheter and the internal clip chambers a closed fluid circuit, and on the other hand of means keeping said reservoir in at least two states, one of higher capacity and corresponding to the teeth being deflated and to their passive position, the other of lesser capacity corresponding to said teeth being inflated and to their active position.

The fluid being used preferably is a liquid because of its incompressability; it a radio-opaque liquid is selected, the clip can be easily located by a mere radiological examination and it is thus possible to ascertain at any time the state of the teeth (active or passive position) by the observed contrast density.

The remote control hydraulic (or possibly pneumatic) member can be housed underneath the skin of the patient (in the manner of the so-called pacemaker cardiac stimulator) when the clip is being put in place; it can subsequently be actuated to control the retraction of the teeth or a new advance by a slight superficial intervention with local anesthesia without operating at the level of the vena cava or manipulating the emplaced clip.

Furthermore, in another feature of the invention, the clip is provided with a closing strip hinging at the free end of an arm and comprising a snap-in means capable of cooperating with a conjugate member located at the free end of another arm for the purpose of closing the clip.

Therefore the clip is closed far more easily and rapidly than the prior clips requiring ligature.

In another implementation of the invention, it is also possible to close the clip by one or several closing teeth located near the free ends of the arms and designed to be inflated simultaneously with the other teeth; each closing tooth consists of a membrane made of a flexible material that will only oppose a negligible impedance to inflation while the membranes forming the other teeth are provided with an elastic inside layer acting against inflation impedance and an outer inextensible layer limiting the spread of said teeth; By applying a suitable pressure within the inside chambers of the clip, it is possible thereby to deflate the operational teeth while keeping the closing teeth in the inflated and hence closed position.

The invention extends to the inherent components of the described device and in particular to a novel occluding clip comprising retractable teeth and if called for to a snap-in closing strip or closing teeth.

The invention outlined above will be better understood when reading the description below and when inspecting the attached drawings showing in non-limiting, illustrative manner several embodiment modes; these drawings are an integral part of the present invention.

FIG. 7 is a bottom-view of a cross-section of the device in place, with respectively the retracted teeth in the passive position and the teeth advanced in the active position, with corresponding states of the vena cava;

FIGS. 8a and 8b are schematic sections of the device in place, with respectively the retracted teeth in the passive position and the teeth advanced in the active position, with corresponding states of the vena cava;

FIG. 9 is a section of a variation of the clip;

Figure 2:
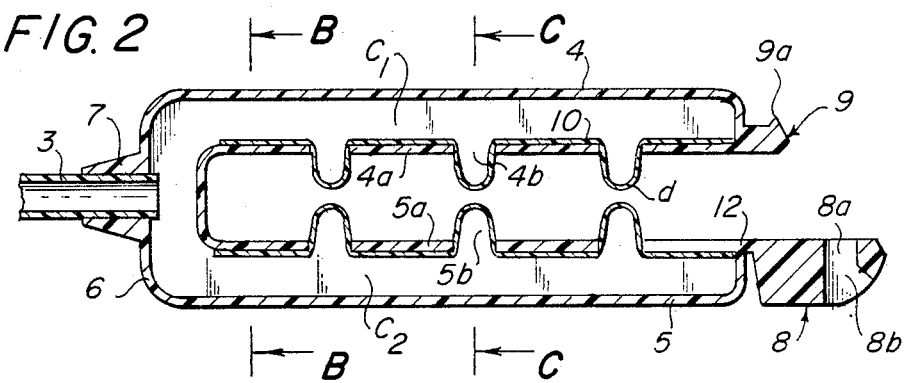
FIG. 2 is a longitudinal section through an axial plane A of the clip of this device.
Figure 3:
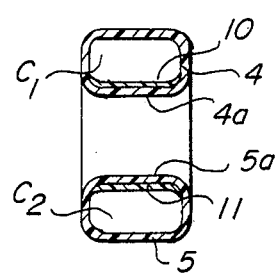
FIGS. 3 and 4 are cross-sections in planes BB and CC of this clip.
Figure 4:
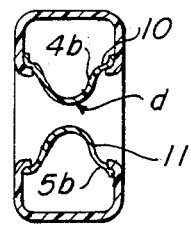

It should be noted that except for FIG. 7, the figures are shown on an expanded scale; to illustrate the dimensions, the sections of FIGS. 2, 3, 4, 5, 11 and 12 were drawn on a scale slightly less than that of FIG. 4.

DESCRIPTION OF THE PREFERRED EMBODIMENTS

The illustratively shown partial occlusion device of FIGS. 1, 2, 3, 4 and 5 essentially comprises three operational sets: a clip 1 which shall straddle a vessel, in particular the inferior vena cava of a patient, a hydraulic control 2 and a catheter 3 connecting the clip 1 and the hydraulic control 2.

The clip 1 comprises two hollow arms 4 and 5 parallel to each other and joined by a hollow U-part 6 so the assembly is in the form of a U-shaped tuning fork.

Each hollow arm has a substantially rectangular cross-section, as shown in FIG. 3 and bounds an inside chamber C1 or C2, these chambers communicating by the hollow U-shaped part 6 and being closed at the other end.

The U-shaped part 6 is provided at its end with a connector fitting 7 to which is connected the catheter 3; the connection may be by bonding.

Furthermore, the free ends of the arms 4 and 5 are provided with clip closing means 8 and 9 described further below.

The arms 4 and 5 comprise compression walls 4a and 5a which are substantially planar and which make outside contact with the wall of the vena cava, which they straddle after the clip has been put in place.

These compression walls 4a and 5a are provided with apertures such as 4b and 5b, for instance three per arm and regularly arrayed along these arms to form four approximately equal intervals. Clearly the number of apertures may be different, in particular it may be two or four per arm depending on the clip dimensions (which will depend on the size of the vessel to be cared for).

The above described clip can be molded in a biocompatible plastic (polytetrafluoroethylene or other) and its walls thicknesses may be such that each arm offers good rigidity while still capable of slightly moving away from or coming closer to the other arm on account of the elasticity obtained from the clip shape.

Figure 1:
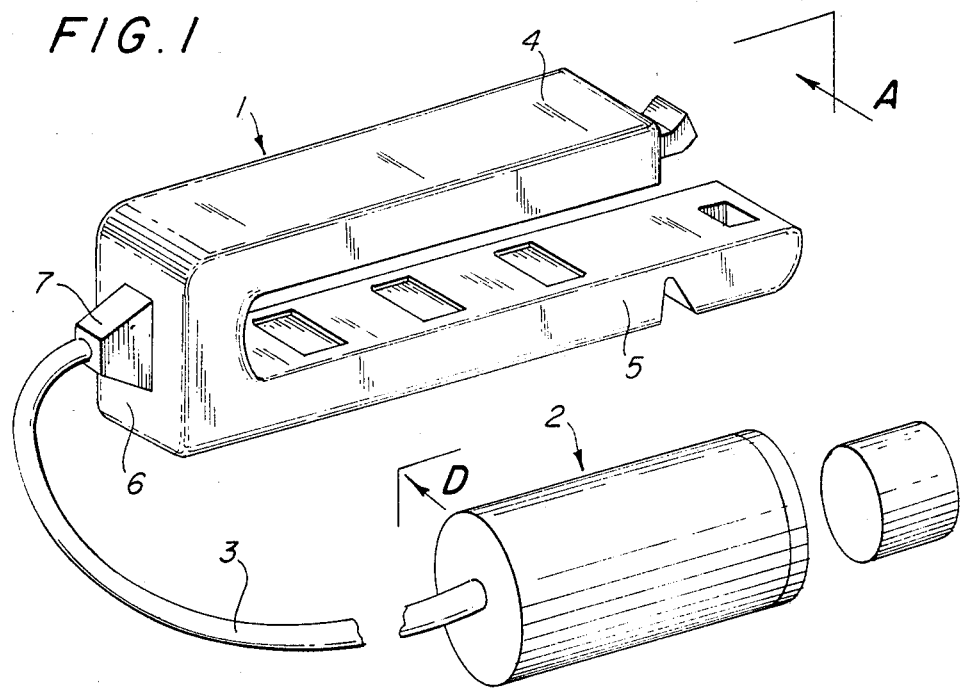
FIG. 1 is a perspective of a first embodiment mode of a partial occlusion device of the invention.

Each arm is provided with a flexible membrane 10 or 11 bonded to the inside of its compression wall and sealing the above cited apertures to render the chambers C1 and C2 impermeable. Each membrane 10 or 11 is of such a shape near each aperture that it can either be inflated to assume the shape of a projecting tooth such as d (FIGS. 2 and 4) or that it can be deflated to withdraw to near the corresponding compression wall 4a or 5a (FIG. 1).

In the described example, each membrane is made of a flexible, non-stretching material whereby the tooth expansion volume is limited.

Furthermore the apertures 4b and 5b of the two arms are located opposite each other to form teeth d also located opposite one another; near the teeth, the flexible and inextensible layer of each membrane is fitted so that the tips of the opposite pairs of teeth when in the active advanced position will be located one near the other without however making contact. The distance between the tips of the advanced teeth is made to be approximately equal to the thickness of the wall of the vessel which must be treated so as to avert local necrosis by crushing said walls.

The clip dimensions of the invention may be of the same order of magnitude as those of the ADAMS & DE WEESE clip; however the width of the arms preferably shall be about 5 mm so that once in place, the clip shall be stable (without the danger of rotating about itself) while nevertheless easy to house in the retroperitoneal space before the spine.

The clip closing means include on one hand a closing strip 8 hinging on the free end of the arm 5 and comprising a snap-in means 8a, and on the other hand a conjugate member 9 located at the free end of the other arm.

In this embodiment, the member 9 consists of a stud provided with an upper beak 9a and the strip 8 comprises an aperture 8a designed to receive the stud 9 when said strip is pushed onto the other arm. This aperture 8a is of such a size that when a snap-in pressure is applied, the stud 9 and its beak 9a can pass through, and it also comprises a clearance 8b where this beak 9a is housed at the end of the snap-in operation.

Such means permit the surgeon to easily and rapidly close the clip after it has been put in place on the vein in order to fix it in place without there being the risk of accidental dislodgement.

It should be noted that these closing means are designed to fully lock the two arms with respect to each other so that they are strictly prevented from nearing or moving away from each other.

In the embodiment shown in FIGS. 1 and 2, the closing strip 8 hinges on the arm 5 by a flexible strap 12 extending said strip 8 and joined to the arm 5. The thickness of this strip is made such that it has the required elasticity, taking the material used into account.

This embodiment mode makes it possible to mold in one step the arms and the closing means.

The second operational set of the device of the invention consists of the catheter 3, conventional per se, and at least 30 cm long, fitted to the size of the patient.

Figure 5:
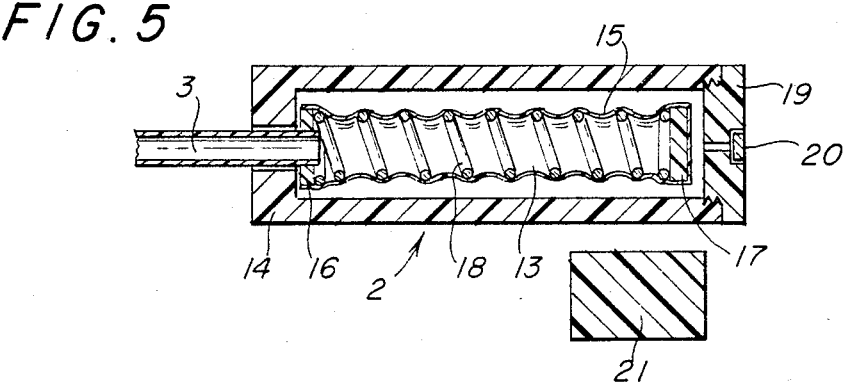
FIG. 5 is a longitudinal section through an axial plane D of the remote control for the device.

FIG. 5 shows an embodiment of the hydraulic member 22 which constitutes the third operational set of the device.

This hydraulic member includes a deforming reservoir 13 housed in a case 14. This reservoir 13 is provided by a membrane is generally cylindrical shape and closed at both ends by two small rigid disks 16 and 17; this membrane 15 can advance or retract longitudinally. Membrane 15 contains a spring 18 guiding it and pushing it in the direction of advance.

The disk 16 is perforated by aperture which is impermeably connected, in particular by bonding, to the end of the catheter 3 (which passes through the case 14 by means of appropriate bore).

At its other end the case 14 is provided with a lid 19 screwed onto it and providing a removable bottom; this lid is provided with a valve 20 allowing to evacuate the air inside the case while preventing blood or any other liquid from entering it.

The spring 18 tends to maintain the reservoir in its state of higher capacity (corresponding to the passive position of the clip teeth). Blocking means furthermore are associated with said reservoir to maintain it in the state of low capacity, the spring 18 being compressed. In this example, these means merely are a removable cylindrical block 21 which the surgeon can insert into the case between its bottom 19 and the disk 17 of the reservoir.

The reservoir 13, catheter 3 and the chambers C1 and C2 of the arms 4, 5 form a closed circuit filled with radio-opaque liquid. The reservoir is sized so that in the absence of the block 21, the teeth d of the clip are retracted into the passive position (relaxed state) at the compression walls. When the block 21 is in place, the teeth are pressurized and move into their active position.

It should be noted that several sizes of the clips 1 can be associated with a single type of hydraulic member 2 as described above; it is enough to provide this member with a set of blocks of lengths fitted to assure appropriate pressurization of the teeth depending on how many these are (and depending on the capacity of the clip chambers C1 and C2).

Figure 6A:
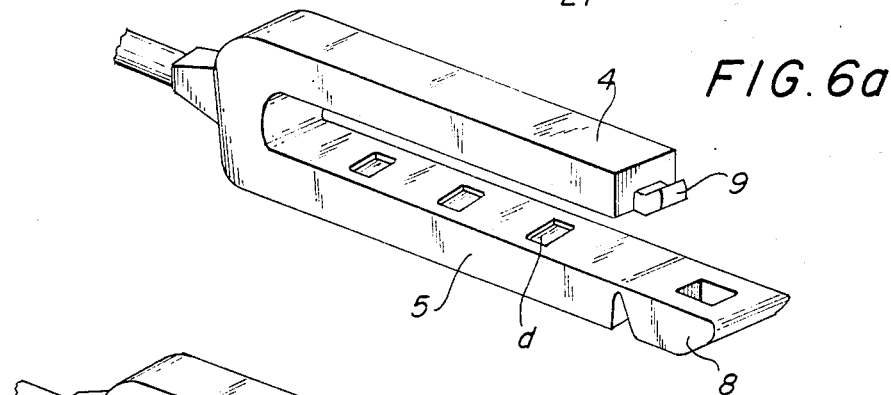
FIGS. 6a, 6b and 6c are schematic perspectives of the three operational states of the clip.
Figure 6B:
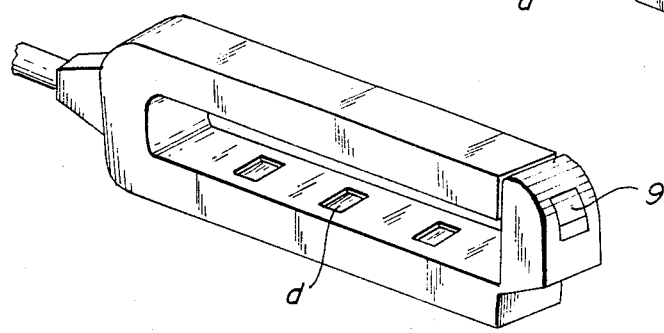
Figure 6C:
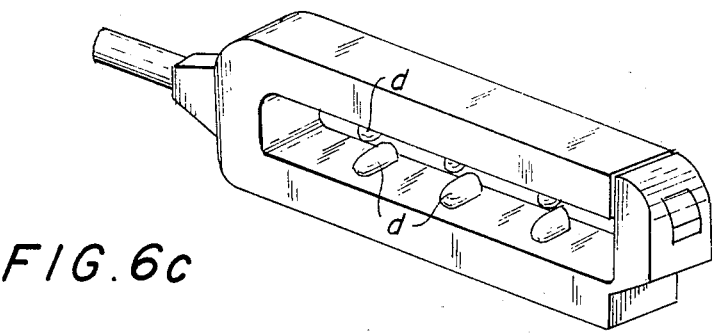

The FIGS. 6a, 6b and 6c show the clip of the invention, respectively (1) when put in place on the vein, the teeth d being retracted and the strip 8 in the extension of the arm 5, (2) after emplacement but before the hydraulic member is actuated, with the teeth d retracted and the strip 8 bent and snapped into the stud 9, following the actuation of the hydraulic member, with the teeth d projecting.

FIG. 7 is a schematic of the clip 1 in place on the inferior vena cava of a patient upstream of the issue of the renal veins; the hydraulic member 2 is housed underneath the teguments so that later it can be easily handled by light intervention with local anesthesia.

After the clip is in place, the surgeon actuates the hydraulic member 2 by inserting the block 21 into its case: the clip is then in the partial-occlusion position as indicated schematically by FIG. 8b; the internal aperture of the vena cava is divided into several channels of lesser bores and the dangers of serious embolism are averted.

At the end of the embolism period, the hydraulic member 2 is actuated in the reverse direction (by removing the block 21) and the teeth d are returned near the compression walls by the depressurization in the chambers C1 and C2 of the arms (FIG. 8a).

It should be noted that the reservoir 13 is brought back into its high-capacity state progressively under the influence of the spring 18, whereby the return of the teeth into the passive position also takes place progressively; the spring constant of this spring 18 is designed to assure this return (that is, to be sufficient to overcome the adhesion forces of the walls of the vena cava) while ensuring said return in a slow enough manner to avert any trauma to the vein.

The significance of the invention, namely to eliminate the effects from clip 1 without having to remove it or maul it, at the end of the embolic period, speaks for itself.

Clearly the sets constituting the device of the invention can also assume other embodiments.

For instance FIG. 9 shows a clip similar to the preceding one but provided with an elastic string 25 to put the clip in place which is connected to the free end of its closing strip. This string has a length of about 16 cm (or more) and serves to facilitate clip emplacement; it will be cut once the clip is in place and closed.

Figure 10:
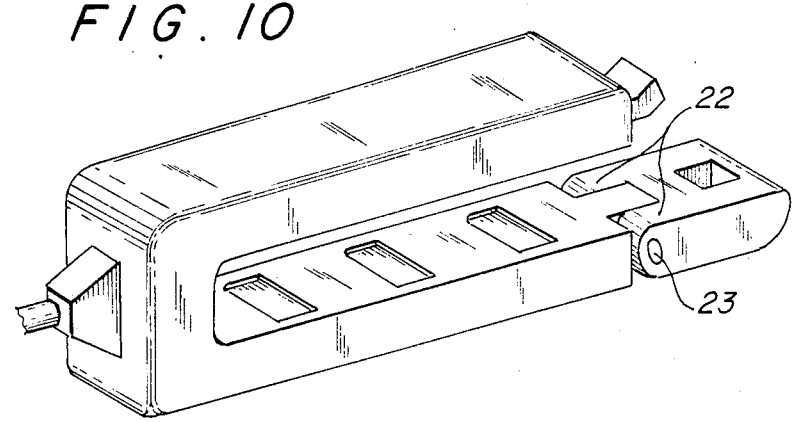
FIG. 10 is a perspective of another embodiment of the clip.
Figure 11:
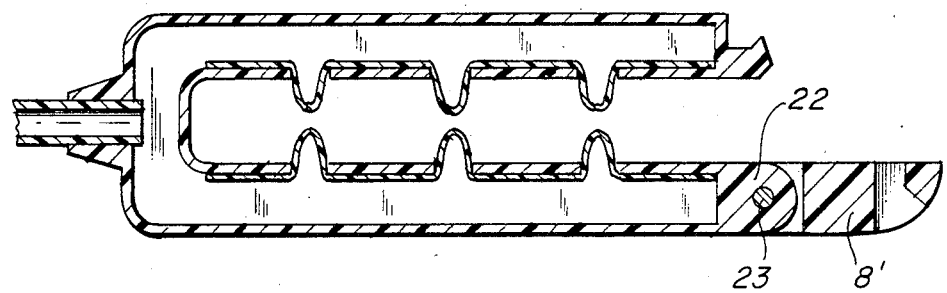
FIG. 11 is an axial section of this embodiment.

FIGS. 10 and 11 show a clip similar to the preceding ones but wherein the closing strip 8' is a separate part hinging on the corresponding arm by a fork 22 and a hinging shaft 23.

Figure 12:
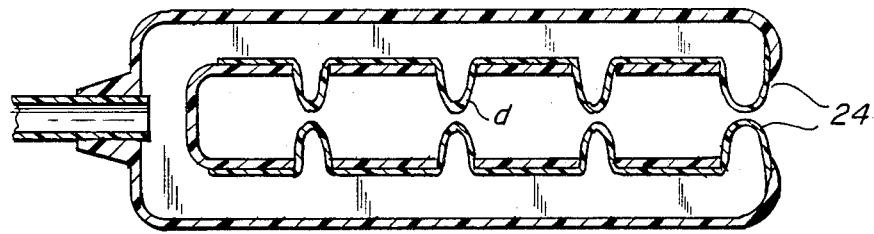
FIG. 12 is an axial section of another embodiment.

FIG. 12 shows another embodiment wherein the clip is closed by two special teeth 24 which are called closing teeth and are located opposite one another near the free end of the clip arms.

These closing teeth 24 are designed similarly to the operational teeth d by flexible membranes which may inflate or deflate at the apertures of the compression walls.

In this example, the membranes forming the closing teeth consist of a layer of a non-stretching and inelastic material so there will be only trivial impedance to inflation; in the inflated state, these closing teeth will rest one against the other to act as closing means as did the strip 8 in the above embodiments.

The membranes forming the other teeth (operational teeth d) consist of two superposed layers: an inside elastic layer capable of impeding inflation, and an outer inextensible layer capable, as previously, to limit the operational volume of the teeth.

The hydraulic member is similar to that already described but, for each clip size, it is associated with two blocks of different lengths so as to set up three pressure conditions in the device:

a depressurization state of the clip, in which the teeth are retracted (equivalent to the state of FIG. 6), a partial pressurization state of the clip for which only the closing teeth 24 are projecting, the pressure being insufficient to overcome the elastic impedance of the other teeth (this state is equivalent to that of FIG. 6b), lastly, a full pressurization state of the clip, for which the pressure suffices to project the operational teeth d (this state is equivalent to that of FIG. 6c).

At the end of the embolism period, the longer block is replaced by the shorter block whereby the clip passes from the third state into the second. The first state is only for emplacing the clip (or very rarely to remove it in case there is an unusual prescription to ablate it).

It must also be noted that the device of the invention can be used to progressively regulate the vascular flow. It only requires to that end to include remote controls designed to move progressively the teeth between their so-called active position, wherein they fully project, and their passive position. This displacement can be implemented in continuous or discrete manner, in steps (in particular using a set of blocks in the embodiment mode described). Clearly too these controls can be fitted to be triggered outside the body without any surgical intervention.

I claim:

1. A device for partly occluding a vessel comprising a clip (1) having a pair of arms for straddling the vessel and being provided with teeth (d) for the purpose of partitioning the inside of the vessel into a plurality of channels, said teeth (d) being retractable, remote control means for moving said teeth between an active position wherein said projecting teeth (d) partition the vessel and a passive position wherein said teeth are withdrawn and without significant harmful effect on the vessel.

2. A partial occlusion device as in claim 1, wherein said clip (1) comprises two arms (4, 5) arranged in a substantially U-shape, said arms comprising compression walls (4a, 5a) opposite one another and for making contact with the vessel, at least one of said arms (4, 5) of said clip being hollow and forming an inside chamber (C1, C2), the compression wall (4a, 5a) of each hollow arm being provided with apertures (4b, 5b), at least one flexible membrane (10, 11) in each of said chambers for sealing the apertures (4b, 5b) of the compression walls, said membrane(s) being designed so as to project through said apertures upon inflation in order to form said teeth (d) in their active position or to deflate and retract into the compression wall to provide the passive position of said teeth, said remote control means including means (2) for pressurizing and depressurizing the inside chamber of each hollow arm and means for actuating the inflation or deflation of the teeth.

3. A partial occlusion device as in claim 2, and wherein said clip arms (4, 5) are hollow and form two hollow inside chambers (C1, C2) connected by a hollow connecting portion (6), each of said walls (4a, 5a) opposite said clip arms including apertures (4b, 5b) and at least one flexible membrane (10, 11) for forming teeth on each of said walls.

4. A partial occlusion device as in claim 3, and wherein said membranes (10, 11) and said apertures (4b, 5b) of the compression walls are positioned so as to form teeth (d) which are paired in opposition to each other.

5. A partial occlusion device as in claim 4, and wherein said membranes (10, 11) comprise a layer of an inextensible, flexible material designed so that the tips of the mutually opposite pairs of teeth when in the active position will be near each other but without making contact.

6. A partial occlusion device as in claim 2, and wherein said remote control means comprises a catheter (3) connected to the inside chamber (C1, C2) of each said arm, and a pneumatic or hydraulic member (2) connected to the other end of said catheter and designed for pressurizing or depressurizing said chambers.

7. A partial occlusion device as in claim 6 and wherein said catheter (3) is connected to the hollow U-shaped portion (6) of said clip.

8. A partial occlusion device as in claim 6 and wherein said pneumatic or hydraulic member comprises a deforming fluid reservoir (13) of variable capacity forming together with said catheter (3) and said chambers (C1, C2) of said clip a closed circuit, hand means (14, 18, 19, 21) for maintaining said reservoir in two states, one of higher capacity corresponding to the deflation of the teeth (d) and to their passive position, the other of lesser capacity corresponding to the inflation of said teeth and to their active position.

9. A partial occlusion device as in claim 8 and wherein said reservoir (13) comprises a membrane (15) of a generally cylindrical shape, closed at its ends and capable of longitudinally advancing or retracting, a spring (18) associated with said membrane for guiding said membrane and pulling said membrane in the direction of advance in order to keep the reservoir in its state of higher capacity, and limiting means (14, 19, 21) associated with said reservoir for maintaining said reservoir in its state of lower capacity.

10. A partial occlusion device as in claim 9 and wherein said reservoir (13) is housed in a case (14) having a removable bottom (19), at least one removable block (21) being provided for insertion between the case bottom and the reservoir for maintaining said reservoir in its state of low capacity.

11. A partial occlusion device as in claim 8 and wherein said closed fluid circuit comprises said reservoir (13), said catheter (3) and said chambers (C1, C2) filled with a radio-opaque liquid.

12. A partial occlusion device as in claim 2 and including means for locking the ends of said arms with respect to each other to prevent relative movement of said arms toward or away from each other.

13. A partial occlusion device as in claim 12 and wherein said locking means comprises a closing strip (8, 8') hinging on the end of one of said arms (5) and having a snap-in member (8a) cooperating with a conjugate member (9) located at the free end of the other of said arms (4) for closing said clip.

14. A partial occlusion device as in claim 13 and wherein said strip (8) hinges on said one of said arms (5) by a flexible strap (12) integral with said one of said arms.

15. A partial occlusion device as in claims 12 and wherein said strip (8') is a separate piece hinged on the arm (5) by a fork (22) and a hinge shaft (23).

16. A partial occlusion device as in claim 12 and wherein said the strip is provided at its free end with a flexible emplacing string (25).

17. A partial occlusion device as in claim 2 and wherein at least one of said arms includes a tooth (24) at the free end thereof for closing the clip.

18. A partial occlusion device as in claim 17 and wherein said clip arms (4, 5) comprise two closing teeth (24) located opposite each other and designed to rest against each other upon inflation.

19. A partial occlusion device as in claim 18 and wherein each closing tooth (24) comprises a membrane made of a flexible material such that it will only offer negligible impedance to inflation, while the membranes forming the other teeth (d) comprise an inside elastic layer for limiting the volume of advance of said teeth.

* * * * *